United States Patent [19]

Aebischer et al.

[11] Patent Number: 5,011,486
[45] Date of Patent: Apr. 30, 1991

[54] COMPOSITE NERVE GUIDANCE CHANNELS

[75] Inventors: Patrick Aebischer, Barrington; Anastassios N. Salessiotis, Providence, both of R.I.

[73] Assignee: Brown University Research Foundation, Providence, R.I.

[21] Appl. No.: 273,236

[22] Filed: Nov. 18, 1988

[51] Int. Cl.$^5$ ............................ A61B 17/00; A61F 2/04
[52] U.S. Cl. ........................................ 606/152; 623/1; 623/12
[58] Field of Search .................. 128/334 R; 623/12, 1; 530/390, 391, 326; 606/152

[56] References Cited

U.S. PATENT DOCUMENTS

| | | | |
|---|---|---|---|
| 3,786,817 | 1/1974 | Palma | 128/334 |
| 3,833,002 | 9/1974 | Palma | 128/334 |
| 3,916,905 | 11/1975 | Kuhn | 128/334 |
| 4,182,262 | 1/1980 | Everson et al. | 118/44 |
| 4,185,095 | 1/1980 | Young | 424/177 |
| 4,287,184 | 9/1981 | Young | 424/177 |
| 4,407,744 | 11/1983 | Young | 260/112 |
| 4,609,546 | 9/1986 | Hiratani | 424/83 |
| 4,669,474 | 6/1987 | Barrows | 128/334 C |
| 4,778,467 | 10/1988 | Stenaas et al. | 623/12 |
| 4,785,059 | 11/1988 | Fydelor et al. | 525/301 |
| 4,785,079 | 11/1988 | Gospodarowicz et al. | 530/399 |
| 4,822,352 | 4/1989 | Joh et al. | 623/1 |
| 4,878,913 | 11/1989 | Aebischer et al. | 623/12 |

OTHER PUBLICATIONS

Gospodarowicz et al., (1986) Cell Differentiation, vol. 19, pp. 1–17.
da Silva et al., (1985) Brain Research, vol. 342, pp. 307–315.
Longo et al., (1983) Experimental Neurology, vol. 81, 756–769.
Nyilas et al., (1983) Trans. Am. Soc. Artif. Intern. Organs, vol. XXIX, pp. 307–313.
Seckel et al., (1983) Plastic and Reconstructive Surgery, vol. 74, No. 2, pp. 173–181.
Uzman et al., (1983) Journal of Neuroscience Research, vol. 9, No. 3, pp. 325–338.
Lumdborg et al., (1982) Journal of Neuropathology and Experimental Neurology, vol. 41, No. 4, pp. 412–422.
Molander et al., (1982) Muscle & Nerve, vol. 5, pp. 54–57.
Politis et al., (1982) Brain Research, vol. 253, pp. 1–12.
Langer (1981) Methods in Enzymology, vol. 73, pp. 57–75.
Midgley et al., (1968) Surgical Forum, vol. 19, pp. 519–520.
Ducker et al., (19) "Experimental Improvements in the Use of Silastic Cuff for Peripheral Nerve Repair", in *Improvements in Silastic Cuffing*, pp. 582–587.

Primary Examiner—Stephen C. Pellegrino
Assistant Examiner—Gary Jackson
Attorney, Agent, or Firm—Thomas J. Engellenner; Ann-Louise Kerner

[57] ABSTRACT

Medical devices and methods employing biocompatible polymers and nerve growth-enhancing active factors are disclosed for use as guidance channels for regenerating nerves. The devices are formed from a porous, tubular membrane containing active factor incorporated within the membrane and having openings adapted to receive the ends of the severed nerve. In one aspect of the invention, the membrane has an impermeable, outer membrane surface and a porous, inner membrane surface through which the active factor can diffuse and which defines the boundary of a lumen through which said nerve may regenerate. Methods for fabricating such devices are also disclosed.

9 Claims, 5 Drawing Sheets

COMPOSITE NERVE GUIDANCE CHANNELS

BACKGROUND OF THE INVENTION

The technical field of this invention concerns medical devices useful for the repair of severed nerves and methods for fabricating and using such devices for nerve repair.

The problem of repairing severed nerves is a long-standing one that has plagued surgeons for over a hundred years. Despite advances in microsurgical techniques, the recovery of a patient from a serious wound is often limited by the degree of nerve damage which cannot be repaired. The replanting of amputated fingers and limbs is especially limited by poor nerve regeneration.

When a nerve is severed, the functions supplied by that nerve, both motor and sensory, are lost. The appendages of the nerve cells, or axons, in the distal regions of the severed nerve, or those areas furthest from the spinal cord, degenerate and die, leaving only the sheaths in which they were contained. These sheaths, too, degenerate with time. The axons in the proximal stump that remain connected to the spinal cord or dorsal root ganglion also suffer some degeneration.

However, degeneration generally does not proceed to the death of all of the nerve cell bodies. Moreover, if the injury occurs far enough from the nerve cell bodies, regeneration will occur. Axonal sprouts will appear from the tip of the regenerating axon. These sprouts grow distally and attempt to reenter the intact neurilemmal sheaths of the distal portion of the severed nerve. If entry is successfully made, axonal growth will continue down these sheaths and function will eventually be restored.

In the conventional approach to nerve repair, an attempt is made to align the cut ends of the fascicles (nerve bundles within the nerve trunk). A similar approach is taken with smaller nerves. In either case, the chief hazard to the successful repair is the trauma produced by the manipulation of the nerve ends and the subsequent suturing to maintain alignment. The trauma appears to stimulate the growth and/or migration of fibroblasts and other scar-forming connective tissue cells. The scar tissue prevents the regenerating axons in the proximal stump from reaching the distal stump to reestablish a nerve charge pathway. The result is a permanent loss of sensory or motor function.

Various attempts have been made over the years to find a replacement for direct (i.e., nerve stump-to-nerve-stump suturing). Much of the research in this field has focused on the use of "channels" or tubular prostheses which permit the cut ends of the nerve to be gently drawn into proximity and secured in place without undue trauma. It is also generally believed that such channels can also prevent, or at least retard, the infiltration of scar-forming connective tissue.

For example, the use of silastic cuffs for peripheral nerve repair was reported by Ducker et al. in Vol. 28, *Journal of Neurosurgery.* pp. 582–587 (1968). Silicone rubber sheathing for nerve repair was reported by Midgley et al. in Vol. 19, *Surgical Forum.* pp. 519–528 (1968) and by Lundborg et al. in Vol. 41, *Journal of Neuropathology in Experimental Neurology*, pp 412–422 (1982). The use of bioresorbable, polyglactin mesh tubing was reported by Molander et al. in Vol. 5, *Muscle & Nerve.* pp. 54–58 (1982). The use of porous acrylic copolymer tubes in nerve regeneration was disclosed by Uzman et al. in Vol. 9, *Journal of Neuroscience Research.* pp. 325–338 (1983). Bioresorbable nerve guidance channels of polyesters and other polymers have been reported by Nyilas et al. in Vol. 29, *Transactions Am. Soc. Artif. Internal Organs.* pp. 307–313 (1983) and in U.S. Pat. No. 4,534,349 issued to Barrows in 1985.

Despite the identification of various materials which can serve as nerve guidance channels, the results of research to date have revealed significant shortcomings in such prostheses. For example, some of the materials identified above have lead to inflammatory reactions in the test animals and have failed to exclude scar tissue formation within the channels. The total number of axons, the number of myelinated axons, the thickness of the epineurium, and the fascicular organization of nerves regenerated within guidance channels are all typically less than satisfactory and compare poorly with the original nerve structure of the test animals. Moreover, the loss of sensory or motor function is still the most common outcome of such laboratory experiments. In addition, if the gap distance separating the nerve stumps is too great, regeneration will not occur.

Channels have been manipulated in various ways in an attempt to correct these shortcomings. For example, channels prefilled with a laminin gel (as disclosed in Madison et al., Vol. 44, *Brain Res.,* pp. 325–334 (1985)), a glycosaminoglycan template (as described in Yannas et al., Vol. 11, *Trans. Soc. Biomat.,* pp. 146 (1985)), or with fibrin (Williams et al., Vol. 264, *J. Como. Neurol.* pp. 284–290 (1987)) have been used to enhance the regeneration of nerve ends separated by a gap distance greater than 10 mm. However, because these substances are normally substrate-bound materials, their conformation and, hence, their level of activity is decreased when they are solubilized.

Channels have also been preloaded with various growth factors (Politis et al., Vol. 253, *Brain Res.* pp. 1–12 (1982)). However, these factors typically are not stable in an aqueous environment; their half lives are measured in hours rather than in weeks, which is the least amount of time usually required for completed regeneration. In addition, the delivery of these factors is not continuous or controlled; it is dispensed as a one time bolus which is not conducive for long term nerve growth stimulation.

There exists a need for a better materials and methods for formation of nerve guidance channels. Materials and methods for nerve repair that would minimize surgical trauma, maximize distances over which nerves can regenerate, prevent interference with nerve growth by scar tissue and improve the chances for successful recovery of sensory or motor function would satisfy a long-felt need in this field.

SUMMARY OF THE INVENTION

It has been discovered that nerve guidance channels containing diffusible nerve growth-inducing active factors can greatly promote the regeneration of severed nerve ends over relatively large distances. These channels consist of biocompatible, porous, tubular membranes having active factor incorporated into the membrane. The factors are released at a controlled rate, thereby prolonging the stimulatory properties of the channel. In addition, factors incorporated into the channel walls have a greater half life than those which are in soluble form within the lumen of the channels; factors sequestered within the hydrophobic environment of the channel wall are not exposed to proteases in the aqueous environment until they are released.

The term "nerve" is used herein to mean both monofascicular and polyfascicular nerves. The same general principals of regeneration within the nerve guidance channels of the present invention are applicable to both.

The term "active factor" is used herein to describe any diffusible substance having bioactivity. In a preferred aspect of the invention, the active factor is a "nerve growth enhancer," such as, for example, a growth factor or active analog, fragment, or derivative thereof.

In one illustrated embodiment, the nerve guidance channels of the present invention are designed to retain active factor within the membrane. The inner surface of the membrane is permeable to the active factor incorporated therein, while the outer membrane surface is impermeable to the factor.

The invention further encompasses methods of repairing a severed nerve using the guidance channels of the present invention. In these methods, the severed nerve ends are placed in proximity to each other and secured within the lumen of the membrane.

Also disclosed are methods of fabricating the device useful in regenerating a severed nerve. In one embodiment, a mandrel having the dimensions of the desired nerve guidance channel can be employed to fabricate the device. One or more coats of a first solution, containing a biocompatible polymer, an active factor, and a hydrophilic carrier, is applied to the mandrel. The hydrophilic carrier establishes domains within the polymer, creating an interconnected pore structure in the finished device from which the active factor is released into the lumen. In a preferred technique, one or more finishing coats of a second solution containing the same or another biocompatible polymer without the carrier is applied to provide an impermeable or substantially less permeable outer surface. The device is then dried and removed from the mandrel.

The invention will next be described in connection with certain preferred embodiments; however, it should be clear that various changes, additions and subtractions can be made by those skilled in the art without departing from the spirit or scope of the invention. For example, in fabricating the nerve guidance devices of the present invention, a variety of known polymeric molding and extrusion techniques can be substituted for the mandrel-coating methods described herein.

Additionally, although the nerve guidance channels described in the examples below are generally tubular in shape, it should be clear that various alternative shapes can be employed. The lumens of the guidance channels can be oval or even square in cross-section. The guidance channels can also be constructed from two or more parts which are clamped together to secure the nerve stumps. Moreover, polymeric sheet materials containing incorporated active factor can be employed and formed into channels in situ. In such a procedure, the nerve stumps can be placed on the surface of the sheet and secured thereto by sutures, adhesives, or friction. The sheet is then wrapped around the nerve segments, and the resulting channel is closed by further sutures, adhesives, or friction.

BRIEF DESCRIPTION OF THE DRAWINGS

The foregoing and other objects of this invention, the various features thereof, as well as the invention, itself, may be more fully understood from the following description, when read together with the accompanying drawings, in which.

DETAILED DESCRIPTION

Figure 1:
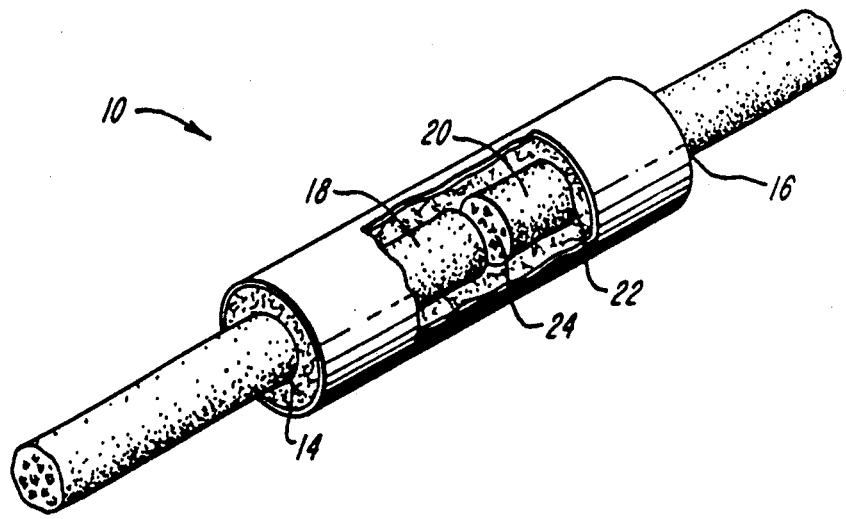
FIG. 1 is a schematic representation of a nerve guidance channel of the present invention.

FIG. 1 shows a nerve guidance device 10, according to the present invention, as a tubular, porous membrane having openings 14 and 16 adapted to receive severed nerve ends 18 and 20. The inner membrane surface 22 defines the boundary of a lumen 24 through which a nerve may regenerate.

Figure 2:
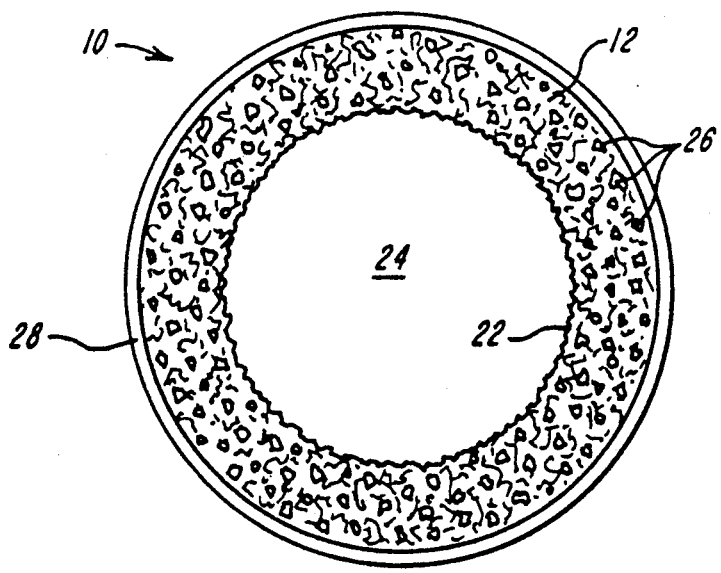
FIG. 2 is a schematic cross-sectional view of the nerve guidance channel of FIG. 1.
Figure 3:
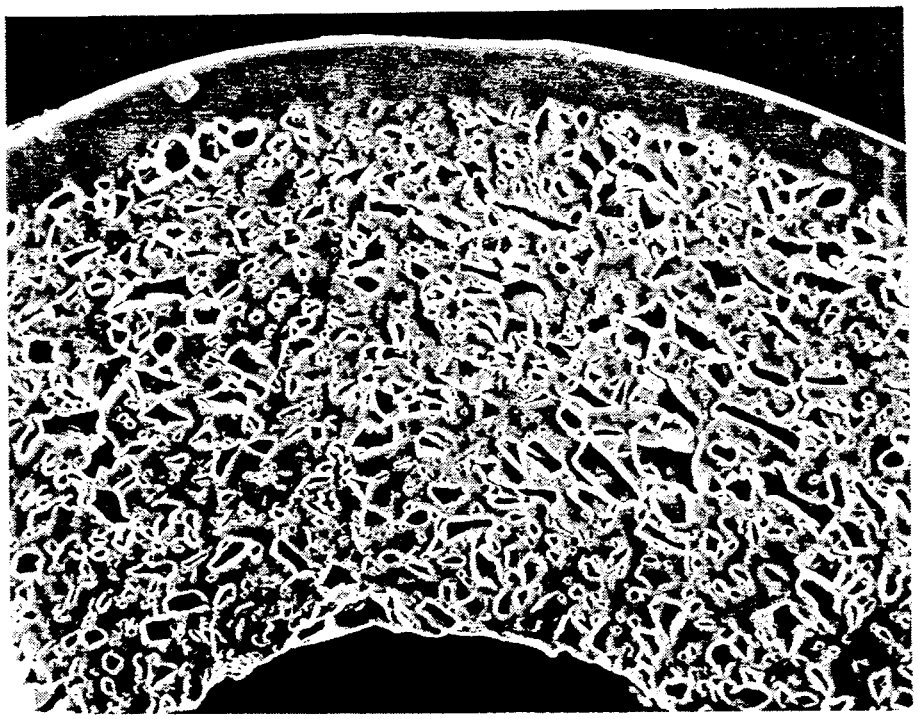
FIG. 3 is an electron micrograph of a cross-section of a nerve guidance channel containing BSA and an active factor.

FIG. 2 is a schematic cross-sectional view of the membrane 10 showing its porous wall structure 12. In this embodiment, active factor 26 is incorporated within the membrane wall 12. The outer membrane surface 28 is nonporous, while porous inner membrane surface 22 allows for the diffusion therethrough of active factor 26. FIG. 3 is an electron micrograph of a cross-section of an actual guidance channel having a nonporous membrane wall and pores containing BSA and active factor.

Various active factors have been found to aid in stimulating and enhancing nerve regeneration. These include alpha 1-acid glycoprotein, various growth factors, second messenger substances, and second messenger inducers. For further details on such active factors and techniques for isolating or producing them, see, for example, Walicke et al., Vol. 83, *Proc. Natl. Acad. Sci. (USA)*, pp. 3012–3016 (1986); Rydel et al., Vol. 1, *J. Neuroscience.* pp. 3639–3653 (1987); Lui et al., Vol. 20, *J. Neurosci. Res.*, pp. 64–72 (1988); and Levi-Montalcini, Vol. 237, *Science,* pp. 1154–1162 (1987), herein incorporated by reference.

Preferable nerve growth enhancers are growth factors, such as nerve growth factor (NGF) and fibroblast growth factor (FGF). Basic FGF (b-FGF) and acidic FGF (a-FGF) are particularly useful for this purpose.

In addition, other nerve growth enhancers, such as second messenger substances or inducers thereof, may be useful. A "second messenger" substance is one that initiates a cellular response to a specific signal external to that cell. Useful second messenger substances include, for example, cyclic adenosine monophosphate (cAMP). Active analogs of cAMP such as 8-bromo cAMP and chlorophenylthio cAMP, or active derivatives and fragments thereof, are also useful. "Second messenger inducers" are responsible for the synthesis or activation of a second messenger substance. Useful second messenger inducers include forskolin, and active derivatives and analogs thereof.

The membrane of the channel may be fabricated from any biocompatible polymers, such as, for example, polyethylene vinyl-acetate (EVA). Alternatively, the channel may be composed of a biocompatible hydrogels, such as polyvinyl pyrolidone, polyethylene oxide (PEO), polyurethanes, acrylates, or mixtures thereof. Preferable acrylates include methacrylates or hydroethylmethacrylates. The membrane instead may be composed of a bioresorbable, biocompatible polymer, such as a polyanhydride, polyester, or mixtures thereof. If the channel is not biodegradable over time, it can be formed with longitudinal lines of weakness to facilitate removal from about the regenerated nerve after healing has progressed sufficiently.

The membrane wall thickness of the nerve guidance channels of the present invention range from about 0.05 to about 1.0 millimeters (mm). Similarly, the diameter of the channel lumen can vary from about 0.5 mm to about 3.0 centimeters (cm), depending upon the size of nerve to be repaired.

In a preferred embodiment of the invention, the outer surface of the membrane is impermeable to solutes of any size, while the inner membrane surface contains pores having a diameter from about 0.1 to 10.0 microns ($\mu$m) so as to be permeable to solutes having a molecular weight of about 100,000 daltons or less. These pores enable the active factors to diffuse out of the membrane and into the lumen of the channel. The particular pore size can be varied depending upon the active factors to be secreted, the size of the nerve to be repaired, and the preferred delivery rate of the active factors.

The invention further encompasses methods of repairing a severed nerve using the nerve guidance channels of the present invention. In these methods, the nerve guidance channels of the present invention as described above, are used by locating the severed nerve ends and selecting and providing an appropriately sized tubular device for the repair. The cut ends of the nerve are gently drawn into channel by manual manipulation or suction, placed in optimal proximity and then secured in position without undue trauma by sutures through the channel, or by a biocompatible adhesive (e.g., fibrin glue) or by frictional engagement with the channel. The channel is then situated in the general in vivo location of the nerve. Antibiotics can be administered to the site, and the wound is then closed.

Also disclosed are methods of fabricating the device useful in regenerating a severed nerve. In one embodiment, a mandrel/molding technique is employed. A cylindrical mandrel having an internal diameter of about 0.05 to 3.00 mm is particularly useful. At least one coat of a first solution containing a biocompatible polymer and an active factor of the type described above is applied to the mandrel. The solution may contain from about 1 to 30%, but preferably about 10% by weight polymer such as, for example, polyethylene vinyl acetate in a solvent. The active factor in the solution may comprise from about 0.001 to 40% by weight of this first solution, depending on the biological activity of the factor and on the desired diffusion rate of the factor from the membrane into the lumen. The remainder of the first solution can comprise a pore-forming, biocompatible agent, for example, a hydrophilic carrier, such as bovine serum albumin, which establishes domains within the polymer, creating an interconnected pore structure in the finished device from which the active factor is released into the lumen. From about 15 to 60 coats of the first solution are applied to the mandrel, with about 24 coats being the most preferable. The coats are then dried, and the resulting device removed from the mandrel.

In a preferred embodiment, at least one coat of an active, factor-free, second solution containing a biocompatible polymer is layered on the first solution-coated mandrel prior to drying and removal from the mold. This second solution may again contain from about 1 to 30% but preferably about 10% by weight biocompatible polymer, such as, for example, polyethylene vinyl acetate without the pore-forming agent. From about 2 to 10 coats of the second solution are applied, with about 4 coats being preferable.

The solvent for the polymer in both the first and second solutions can be any one of a variety of organic solvents, such as, for example, methylene chloride The accumulated coats on the mandrel are then dried and removed from the mandrel to form the guidance channel of the present invention.

This layering procedure allows deposition of an impermeable coat on the outer surface of the device, insuring that the active factors incorporated into the membrane walls will be inhibited from diffusing through the external surface, and will diffuse only through the inner membrane surface into the lumen of the channel.

The invention will next be described in connection with the following examples and experiments.

EXAMPLE 1

Polyethylene vinyl-acetate (EVA) pellets (Elvax-40) were obtained from Dupont (Wilmington, DE). Impurities were removed with multiple wash in pure ethanol and distilled water. A 10% (w/w) solution of EVA was prepared in methylene chloride.

Fabrication took place in a clean room with automated equipment allowing control of processing speed. Tubular guidance devices (50 mm long ×1.5 mm ID ×1.9 mm OD) were prepared by dip molding over of a stainless steel wire mandrel 28 times.

The channels were then dried overnight in a fume hood, cut into 19 mm pieces, and placed under vacuum for 24 hours. Before implantation, the channels were cleaned and sterilized in a 70% ethanol solution.

EXAMPLE 2

Guidance channels containing bovine serum albumin (BSA) (Sigma, St. Louis, Mo) were prepared as described in EXAMPLE 1, except that BSA was added to 10% EVA to obtain a 40% (w/w) BSA/EVA solid matrix upon drying. The mold was dipped 24 times in the BSA/EVA solution, followed by 4 dips in a pure 10% EVA solution. Prior to being put into solution, the BSA was served to obtain particles less than 75 $\mu$m in diameter.

EXAMPLE 3

Guidance channels containing b-FGF and BSA were prepared as described in EXAMPLE 2, except that 100 $\mu$l of b-FGF (recombinant, Amgen, Thousand Oaks, CA) was added to a 10 ml solution 40% (w/w) BSA/EVA, resulting in a 0.004% (w/w) b-FGF/EVA solid matrix upon drying. The mold was dipped 24 times in the b-FGF/BSA/EVA solution, followed by 4 times in 10% pure EVA solution.

EXAMPLE 4

Guidance channels containing $\alpha$1-GP and BSA were prepared as described in EXAMPLE 2 except that $\alpha$1 -GP was added to a 10 ml solution of 40% (w/w) BSA/EVA which resulted in a 4% (w/w) $\alpha$1 -GP/ EVA solid matrix upon drying. The mold was dipped 24 times in the α1-GP/BSA/EVA solution, followed by 4 dips in a pure 10% EVA solution.

EXAMPLE 5

Guidance channels containing b-FGF, αl -GP, and BSA were prepared as described in EXAMPLE 2, except that 100 μl of b-FGF and αl -GP were added to a 10 ml solution of 40% (w/w) BSA/EVA which resulted in a 0.004% (w/w) b-FGF, 4% (w/w) αl -GP solid EVA matrix upon drying. The mold was dipped 24 times in the b-FGF/αl -GP/BSA/EVA solution, followed by 4 dips in a pure 10% EVA solution.

EXAMPLE 6

The kinetics of BSA release in in vitro studies were determined by incubating 6 mm long channels in sterile scintillation vials containing 10 ml saline at 37° C. The solutions were changed daily, and the amount of BSA released per day was monitored at 220 nm using a DU-65 spectrophotometer (Beckman, Fullerton, CA). Percentage cumulative release curves were prepared for each channel. It is assumed that the percentage cumulative release of b-FGF precisely followed that of BSA, as the molecules have similar molecular weight.

Figure 4:
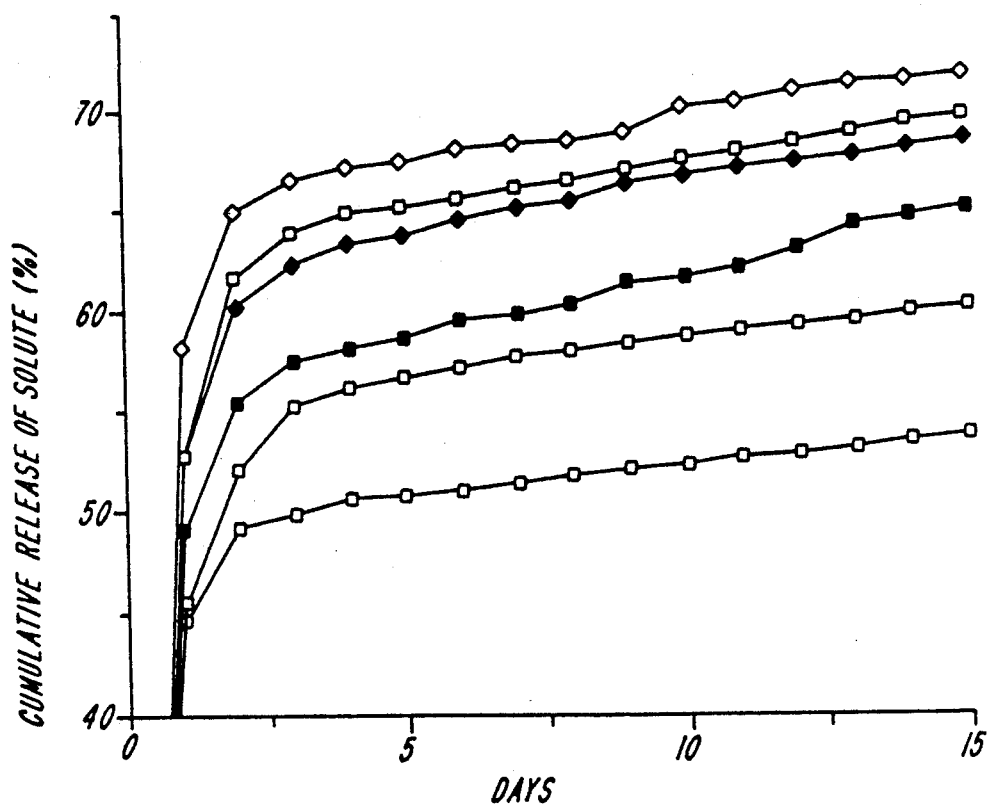
FIG. 4 is a graphic representation of the rate at which a protein is released from the nerve guidance channel of the present invention as a function of time.

FIG. 4 shows the kinetics of active factor release from a nerve guidance channel as demonstrated by the release of BSA, a molecule having the same approximate molecular weight and diffusion characteristics as FGF. The kinetics of BSA release for 6 BSA/EVA channels were found to consist of 2 phases. During the first three days, a burst phase was observed, during which approximately 50% of the total BSA was released from each channel. After three days, all six channels showed a linear pattern of release (zero order kinetics). During the linear phase, the rate of release ranged from 0.1 to 0.5% BSA per day.

The bioactivity of b-FGF released from b-FGF/BSA/EVA channels was assayed in PC12 cell cultures. PC12 is a cell line derived from a pheocromocytoma (Ryel et al., Vol. 1, *J. Neurosci.* pp. 3639–3653, (1987)). polystyrene cultures dishes coated with rat tail collagens were seeded with a $10^5$ PC12 cells per ml. PC12 cells were cultivated for 3 days in RPM1 1640 medium supplemented with 10% heat-inactivated horse serum and 5% heat-inactivated fetal calf serum in general accordance with the procedures of Greene et al., Vol. 147, *Meth Enzymol pp.* 207–216 (1987), incorporated herein by reference. The culture medium was changed every 2 days. Six mm long channels were then placed in each dish. The neurite extension of PC12 cells incubated in vitro with channels releasing either BSA alone or BSA and b-FGF was monitored under phase contrast with a IM35 Zeiss microscope (Zeiss AG., Oberkochen, Federal Rep. Germany) for 6 days.

Figure 5A:
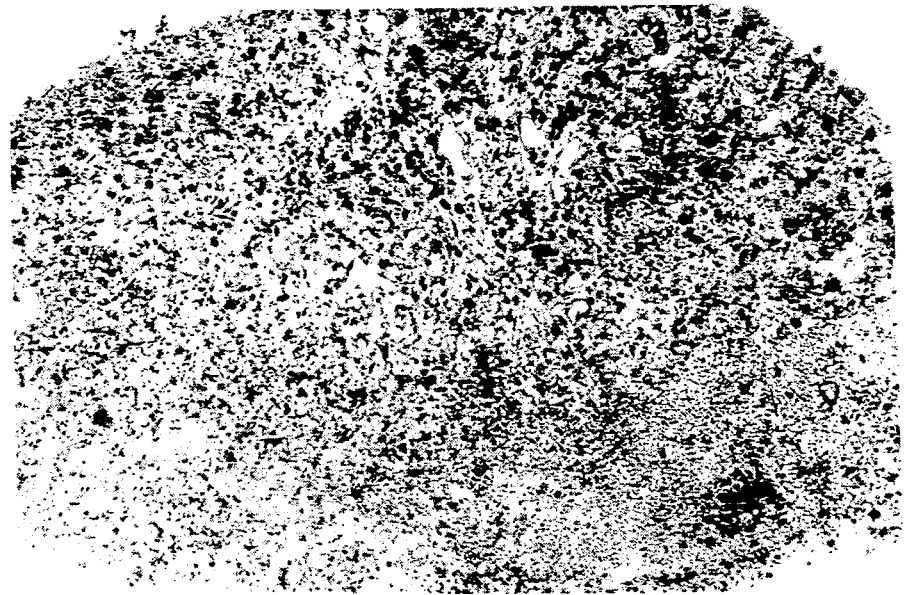
FIGS. 5A and 5B is a phase contrast micrograph of human (PC12) cells cultured in the presence of a control nerve guidance channel releasing BSA only (A), and a channel releasing BSA and b-FGF (B) respectively.
Figure 5B:
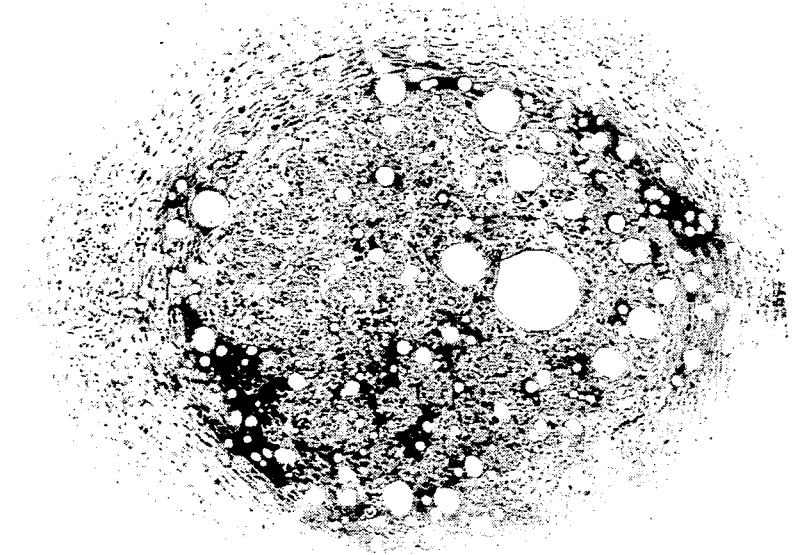

Channels releasing BSA only did not show neurite extension (FIG. 5A), while cells grown in dishes containing channels releasing b-FGF extended neurites after 48 hours and developed an intense network of neurites at 6 days (FIG. 5B). These results suggest that the b-FGF released from the channels was bioactive and that no significant denaturation of the active factor occurred after exposure to the methylene chloride solvent.

EXAMPLE 7

In vivo studies were performed to determine the effectiveness of the nerve guidance channels fabricated as described in EXAMPLES 1-5.

The guidance channels were implanted into rats as follows The left sciatic nerve of Nembutal anesthetized rats is exposed through a skin incision along the anterior medial aspect of the thigh after retracting the gluteus maximus muscle. The sciatic nerve is mobilized from the ischial tuberosity to the tibial-peroneal bifurcation by gently dissecting the overlying connective tissue sheaths. An 8 mm segment of the nerve 1 mm proximal to the tibial-peroneal bifurcation is resected and discarded. The proximal and distal nerve stumps are secured within the 19 mm long guidance channel lumen with a single 10-0 nylon suture. The nerves are positioned 2 mm from the channel ends, separating the proximal and distal stumps by a gap of 15 mm. The surgical site is then irrigated with sterile saline Muscle approximation and skin closure is then achieved with 6.0 monofilament nylon (Ethilon ®) and 6.0 braided silk sutures. A septic surgical technique is maintained throughout the procedure, which is performed with the aid of a Zeiss operating microscope. Cohorts of 6 animals were implanted for 4 weeks with channels made of pure EVA, BSA/EVA, b-FGF/BSA/EVA, αl -GP/BSA/EVA, or b-FGF/αl -GP/BSA/EVA.

The rats were deeply anesthetized with sodium thiopental and then perfused transcardially with 100 ml of phosphate-buffered saline (PBS), followed by 100 ml of fixative 3.0% paraformaldehyde, 2.5% glutaraldehyde in PBS at a pH of about 7.4. The operative site was re-opened, and the guidance channel with 3 mm of native nerve at either end removed.

EXAMPLE 8

Figure 6:
FIG. 6 is a photographic representation of an electron micrograph taken at the midpoint of a guidance channel releasing b-FGF four weeks post-implantation.

Light and electron microscopy served to define the extent of nerve regeneration upon retrieval in in vivo experiments (FIGS. 5–6).

The explants were immediately immersed in fixative, and the guidance channels were cut transversely at their midpoint 24 hours later The specimens were post-fixed in a 1% osmium tetroxide solution, dehydrated, and embedded in Spurr resin. Transverse sections taken at the midpoint of the guidance channel were cut on a Sorvall MT-5000 microtome. Transverse sections are also taken at the level of the native proximal and distal nerve 2 mm away from the channel.

Semi-thin sections (1 μm) for light microscopy were stained with toluidine blue and fuchsin. Ultrathin sections (60–80 nm) for transmission electron microscopy (TEM) were stained with Reynold's lead citrate and uranyl acetate.

Myelinated axon populations, blood vessel numbers, fascicle numbers, axonal diameter, and myelin thickness are counted with the aid of a morphometric analysis system (CUE-2, Olympus Corp., Lake Success, NY) interfaced with an IM35 Zeiss microscope.

All channels exhibited a minimal tissue reaction consisting of the presence of several layers of fibroblasts and connective tissue surrounding the polyer. None of the pure EVA had cables bridging the nerve stumps. BSA/EVA channels contained tissue cables without myelinated or unmyelinated axons, whereas four out of six b-FGF/BSA/EVA channels had nerve cables bridging both nerve stumps. The inclusion of αl -GP to b-FGF/BSA/EVA channels lead to enhanced regeneration. The regenerated cables were circular in shape and surrounded by a viscous gel. They were never seen growing along the inner wall of the channels. General histologic examination of transverse sections taken at the midpoint of the regenerated cable revealed numerous nerve fascicles surrounded by an epineurial sheath. The regenerated cables displayed a very high number of blood vessels. Macrophages lined the regenerated cables and the inner wall of the guidance channel, and presumptive Schwann cells and numerous microfascicles surrounded by perineurial-like tissue were also observed. Numerous unmyelinated axons and myelinated axons at various stages of myelination were also observed (FIG. 6). Two of the nerve cables regenerated in b-FGF releasing channels contained more than a thousand myelinated axons at the midpoint of the channel.

We claim:

1. A medical device for use in regenerating a severed nerve, said device comprising a tubular, biocompatible, porous, polymeric membrane containing an active factor incorporated within the walls of said membrane, said device comprising an impermeable outer membrane surface and porous inner membrane surface through which said active factor may diffuse, and said membrane having openings adapted to receive the ends of said severed nerve, and an inner lumen through which said nerve may regenerate.

2. The device of claim 1 wherein said active factor is alpha 1-acid glycoprotein.

3. The device of claim 1 wherein said active factor is acidic fibroblast growth factor.

4. The device of claim 1 wherein said active factor is basic fibroblast growth factor.

5. The device of claim 1 wherein said biocompatible, polymeric membrane comprises polyethylene vinyl acetate.

6. The device of claim 1 wherein the thickness of said membrane ranges from about 0.05 to about 1.0 millimeter.

7. The device of claim 1 wherein said lumen has a diameter ranging from about 0.5 millimeter to about 3.0 centimeters.

8. The device of claim 1 wherein said porous membranes contains pores having a diameter of about 0.1 to 10.0 micrometers.

9. The device of claim 1 wherein said porous membrane is permeable to solutes having a molecular weight of about 100,000 daltons or less.

* * * * *